United States Patent
Meens

(10) Patent No.: US 9,821,148 B2
(45) Date of Patent: *Nov. 21, 2017

(54) BALLOON CATHETER AND METHOD FOR MANUFACTURING IT

(71) Applicant: C.R. BARD, INC., Murray Hill, NJ (US)

(72) Inventor: Hendrik Jozef Maria Meens, Weert (NL)

(73) Assignee: C.R. BARD, INC., Murray Hill, NJ (US)

( * ) Notice: Subject to any disclaimer, the term of this patent is extended or adjusted under 35 U.S.C. 154(b) by 251 days.

This patent is subject to a terminal disclaimer.

(21) Appl. No.: 14/583,236

(22) Filed: Dec. 26, 2014

(65) Prior Publication Data

US 2015/0112258 A1    Apr. 23, 2015

Related U.S. Application Data

(63) Continuation of application No. 13/783,745, filed on Mar. 4, 2013, now Pat. No. 8,951,279, which is a continuation of application No. 12/978,908, filed on Dec. 27, 2010, now Pat. No. 8,388,641, which is a continuation of application No. 10/140,524, filed on May 7, 2002, now Pat. No. 8,083,761.

(51) Int. Cl.
*A61M 25/10* (2013.01)
*A61F 2/958* (2013.01)

(52) U.S. Cl.
CPC ......... *A61M 25/1002* (2013.01); *A61F 2/958* (2013.01); *A61M 25/1027* (2013.01); *A61F 2002/9583* (2013.01); *A61F 2230/0091* (2013.01); *A61M 25/1038* (2013.01); *A61M 2025/1004* (2013.01); *A61M 2025/1031* (2013.01); *A61M 2025/1086* (2013.01)

(58) Field of Classification Search
CPC .......... A61M 25/1002; A61M 25/1038; A61M 25/1027; A61M 2025/1004
See application file for complete search history.

(56) References Cited

U.S. PATENT DOCUMENTS

| | | | | |
|---|---|---|---|---|
| 4,422,447 A * | 12/1983 | Schiff | ................. | A61M 25/10 600/18 |
| 5,628,754 A * | 5/1997 | Shevlin | ................. | A61F 2/958 606/192 |
| 6,143,016 A * | 11/2000 | Bleam | ................. | A61F 2/958 604/104 |
| 6,478,807 B1 * | 11/2002 | Foreman | ................. | A61F 2/958 606/108 |
| 8,083,761 B2 * | 12/2011 | Meens | ................. | A61F 2/958 606/192 |
| 8,388,641 B2 * | 3/2013 | Meens | ................. | A61F 2/958 606/192 |
| 8,951,279 B2 * | 2/2015 | Meens | ................. | A61F 2/958 606/192 |

\* cited by examiner

*Primary Examiner* — Tuan V Nguyen
(74) *Attorney, Agent, or Firm* — King & Schickli, PLLC

(57) ABSTRACT

A balloon catheter includes a catheter tube and an inflatable balloon. The ends of the balloon are attached to the catheter tube. The outside surface of the balloon in an uninflated state is provided with a relief structure which in an inflated state of the balloon is substantially disappeared. A method for producing such a relief structure is by winding a wire helically around the outer surface of the balloon.

24 Claims, 1 Drawing Sheet

BALLOON CATHETER AND METHOD FOR MANUFACTURING IT

TECHNICAL FIELD

The present invention relates to a balloon catheter comprising a catheter tube and an inflatable balloon which at its ends is attached to the catheter tube. The invention further relates to a method of manufacturing a balloon catheter.

BACKGROUND INFORMATION

Balloon catheters of this type are generally known and are used for dilating vessels and lumina. In order to pass the balloon catheter easily and safely through the vessels and lumina and to position it at the required place for dilatation, it is important that the balloon catheter has a small profile and is sufficiently flexible.

The object of the invention is therefore to provide an improved balloon catheter.

BRIEF SUMMARY OF THE INVENTION

The balloon catheter according to the invention is characterized in that the outside surface of the balloon in an uninflated state is provided with a relief structure which in an inflated state of the balloon is substantially disappeared.

Tests have shown that with a relief structure on the outside surface of the balloon, a catheter is obtained that is more flexible than a standard balloon catheter. The balloon catheter according to the invention can therefore be passed more easily and more safely through vessels and lumina to the point of dilatation. Because of its flexibility, the catheter will be able to adapt better to a bend in a vessel or a lumen, thus reducing the risk of damage to the vessel or lumen.

The required relief structure may have different embodiments, but preferably comprises at least one groove that extends at least transversely in the longitudinal direction of the balloon in order to give the catheter the required flexibility in a direction transverse to the longitudinal direction thereof.

The groove preferably extends at a predetermined angle with respect to the longitudinal direction of the balloon. According to a preferred embodiment the groove extends helically from one end to the other end of the balloon, over the outside surface thereof.

According to another embodiment, the relief structure comprises two or more grooves that extend helically from one end to the other end of the balloon, crossing each other. Tests have shown that with such a relief structure a very flexible balloon catheter is obtained which also has a relatively small profile.

The invention also relates to a method for producing a balloon catheter comprising attaching the ends of an inflatable balloon to a catheter tube, whereby according to the invention the outside surface of the balloon is provided with a relief structure.

According to an embodiment of the invention, the relief structure is produced on the application of heat in order to deform the elastic material of the balloon.

The relief structure is also preferably produced on the surface of the balloon by applying a high pressure to the inside of the balloon.

According to a very inexpensive method, the relief structure is produced on the surface of the balloon by winding a wire around the balloon in the form of a helix.

According to another simple method, the relief structure is produced on the surface of the balloon by taking up the balloon in a counter-pressure body that has the relief structure.

BRIEF DESCRIPTION OF THE DRAWINGS

The invention is explained in more detail on the basis of the drawings attached. The drawings show.

DETAILED DESCRIPTION OF THE INVENTION

A balloon catheter according to the invention comprises a catheter tube 1 and an inflatable balloon 2, which at its ends is attached to the catheter tube 1. In an uninflated state (FIGS. 1A and 2A), the outside surface of balloon 2 has a relief structure 4 that in the inflated state has virtually or completely disappeared (FIGS. 1B and 2B). The relief structure gives the catheter its required flexibility.

Figure 1A:
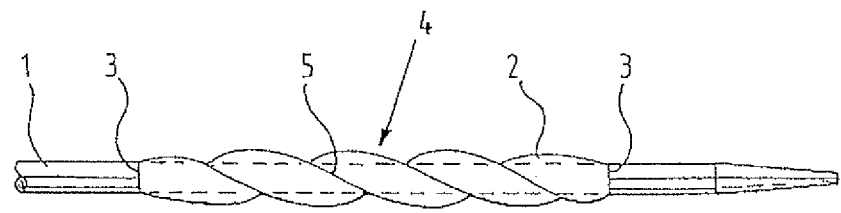
FIG. 1A is a side view of a first embodiment of a balloon catheter in an uninflated state.
Figure 1B:
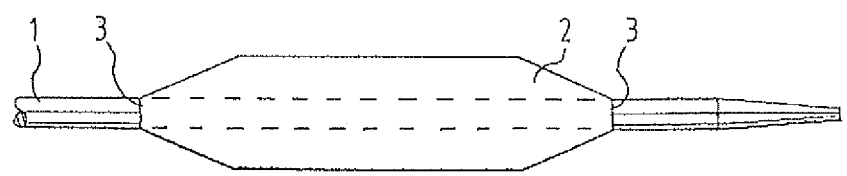
FIG. 1B is a side view of the catheter in FIG. 1A in an inflated state.

In the first embodiment according to FIGS. 1A and 1B, the relief structure 4 consists of one groove 5, which extends helically from one end 3 to the other end 3 of the balloon 2, over the outside surface thereof. The uninflated balloon 2 has thereby obtained a helical relief surface. In the second embodiment according to FIGS. 2A and 2B, the relief structure 4 consists of two grooves 5, 6, which extend helically from one end 3 to the other end 3 of the balloon 2 and thereby cross each other. The uninflated balloon 2 has hereby obtained a padded relief surface.

Other relief structures are of course possible, provided that the relief structure on the catheter creates the necessary flexibility in a direction transverse to the longitudinal direction of the balloon.

Figure 2A:
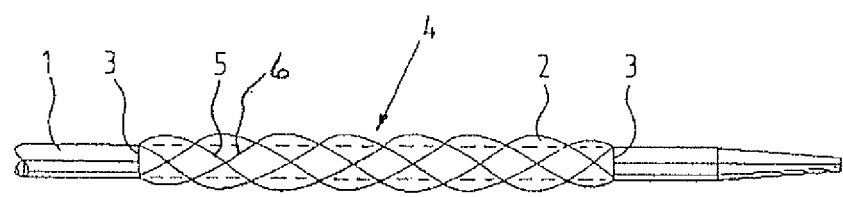
FIG. 2A is a side view of a second embodiment of a balloon catheter in an uninflated state.
Figure 2B:
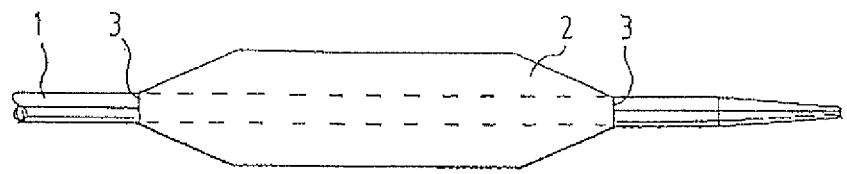
FIG. 2B is a side view of the catheter of FIG. 2A in an inflated state.

One way of obtaining the relief structure as shown in the drawings is by winding a wire helically around the balloon 2. If the wire is wound only in the forward direction, the structure according to FIG. 1A is obtained, and if the wire is also wound in the return direction, the structure in FIG. 2A is obtained. After the wire has been wound around the balloon, a sleeve is pulled over the balloon. Subsequently, with the application of raised pressure to the inside of the balloon, the balloon is heated in such a way that, in an uninflated state, the balloon obtains a relief structure that on dilating of the balloon at the dilatation site in the vessel or lumen will virtually or completely disappear. The sleeve is then removed and the balloon catheter can be inserted into a vessel or a lumen.

Instead of winding a wire, the balloon may be placed in a mould, which is provided with the relief pattern required in order for it to obtain, under raised pressure and temperature, the relief structure required.

Before the balloon is provided with its relief structure, preferably it is folded in the usual way in order to reduce its profile. By applying the relief structure, the profile will be reduced still further as an additional, advantageous effect.

The usual way of folding a balloon mounted on a catheter involves the folding of the uninflated balloon wall so that wall overlaps itself and defines portions of the balloon wall that are within a fold. A folded balloon has exposed portions of the folded balloon that are exposed to an exterior environment of the balloon, and unexposed portions that are not exposed because those portion s are contained within a fold of the folded balloon.

Note that, although it is not shown in the drawings, it is possible to provide the outside surface of the balloon with various helical grooves that cross each other.

What is claimed is:

1. A balloon catheter comprising a catheter shaft and a balloon wall defining a balloon that includes:
   proximal and distal ends each attached to the catheter shaft and disposed on a longitudinal axis, the balloon wall having first, second, and third portions, the second portion including a helical groove between the first and third portions circumferentially about the longitudinal axis to adjoin the first and third portions, the first portion defining a groove therein having an end terminating where the second portion adjoins the first portion, the third portion defining a groove therein having an end terminating where the second portion adjoins the third portion, and the end of the first portion groove proximate to the end of the third portion groove;
   wherein the grooves of the first, second, and third portions are independent of any folds in the balloon and define valleys in the balloon wall separated by peaks in the balloon wall and are substantially disappeared when the balloon is in an inflated state at an intended operating pressure during use, and wherein the valleys remain unoccupied by a stent for deployment when the balloon is in an uninflated and folded state before use in a patient,
   wherein the grooves of the first and third portions are disposed to form a series of aligned grooves extending helically about the axis with a distal end of one of the aligned grooves facing a proximal end of another one of the aligned grooves,
   wherein the second portion defines a folded portion of the balloon.

2. The balloon catheter of claim 1 wherein the balloon has a repeating pattern of second portions disposed between first and third portions circumferentially about the axis.

3. The balloon catheter of claim 1 wherein the series of aligned grooves define a single helix about the axis.

4. The balloon catheter of claim 1 wherein the series of aligned grooves define first and second helixes about the axis.

5. The balloon catheter of claim 4 wherein the first and second helixes intersect each other.

6. A balloon catheter comprising:
   a catheter shaft disposed on a longitudinal axis; and
   a balloon including opposite ends attached to the catheter shaft, and further including an outside surface that, when the balloon is in an uninflated and folded state, comprises a helical groove that is substantially disappeared when the balloon is in an inflated state at an intended operating pressure during use,
   wherein the helical groove remains unoccupied, and
   wherein the balloon in the folded state includes a plurality of circumferential folds, such that at least one first portion of the outside surface is not exposed to the exterior environment and one second portion of the outside surface is exposed to the exterior environment, and
   wherein the groove is present on the second portion of the outside surface, but not present on the first portion of the outside surface.

7. The balloon catheter of claim 6 wherein the balloon further includes a plurality of helical grooves.

8. The balloon catheter of claim 7 wherein the plurality of grooves intersect one another.

9. The balloon catheter of claim 6 wherein the balloon includes a frustoconically shaped section on each of the opposite ends and a barrel shaped section between said frustoconically shaped sections.

10. The balloon catheter of claim 9 wherein the groove extends at least partially along the barrel shaped section.

11. The balloon catheter of claim 10 wherein the balloon further includes a plurality of helical grooves.

12. The balloon catheter of claim 11 wherein the plurality of grooves intersect one another.

13. The balloon catheter of claim 12 wherein the helical groove is independent of the plurality of folds.

14. The balloon catheter of claim 9 wherein the groove extends at least partially along one of the frustoconically shaped sections.

15. The balloon catheter of claim 14 wherein the balloon further includes a plurality of helical grooves.

16. The balloon catheter of claim 15 wherein the plurality of grooves intersect one another.

17. The balloon catheter of claim 16 wherein the helical groove is independent of the plurality of folds.

18. The balloon catheter of claim 6 wherein the helical groove is independent of the plurality of folds.

19. A balloon comprising:
   a balloon wall having an uninflated configuration and an inflated configuration;
   wherein, in the uninflated configuration, the balloon wall overlaps itself to form a plurality of folds, and an outer surface of the balloon wall further includes at least one relief structure comprising a helical groove extending circumferentially around the balloon and along a longitudinal axis of the balloon;
   wherein in the inflated configuration, the plurality of folds and the at least one helical groove is substantially disappeared;
   wherein the helical groove remains unoccupied;
   wherein the balloon is adapted for use with a catheter shaft; and
   wherein the outer surface of the balloon wall within the fold does not include the helical groove and the outer surface of the balloon wall external to the fold does include the helical groove;
   wherein the balloon includes proximal and distal tapered sections and a barrel shaped section between the proximal and distal ends.

20. The balloon of claim 19, wherein the balloon further includes a plurality of helical grooves.

21. The balloon of claim 20, wherein the plurality of grooves intersect one another.

22. The balloon of claim 19, wherein the groove extends at least partially along the barrel shaped section.

23. The balloon of claim 22, wherein the balloon further includes a plurality of helical grooves.

24. The balloon of claim 19, wherein the balloon wall includes a proximal end and a distal end, and wherein the proximal end and the distal end are adapted to attach to the catheter shaft.

* * * * *